United States Patent
Wang

(10) Patent No.: US 6,734,970 B2
(45) Date of Patent: May 11, 2004

(54) METHOD AND A DEVICE FOR DETERMINING THE RADIATION-DAMAGE RESISTANCE OF AN OPTICAL MATERIAL

(75) Inventor: Hexin Wang, Koenigsbronn (DE)

(73) Assignee: Carl Zeiss Semiconductor Manufacturing Technologuies AG, Oberkochen (DE)

(*) Notice: Subject to any disclaimer, the term of this patent is extended or adjusted under 35 U.S.C. 154(b) by 0 days.

(21) Appl. No.: 10/224,391

(22) Filed: Aug. 21, 2002

(65) Prior Publication Data

US 2003/0223065 A1 Dec. 4, 2003

(30) Foreign Application Priority Data

Jun. 4, 2002 (DE) .......................... 102 25 842

(51) Int. Cl.[7] .............................................. G01B 11/00
(52) U.S. Cl. ........................................ 356/388; 356/433
(58) Field of Search ................................ 356/336–343, 356/432–440; 250/574, 282, 423 P

(56) References Cited

U.S. PATENT DOCUMENTS

| | | | | | |
|---|---|---|---|---|---|
| 4,209,697 | A | * | 6/1980 | Renner et al. ............... | 250/282 |
| 4,534,651 | A | * | 8/1985 | Minikane ..................... | 356/440 |
| 4,639,137 | A | * | 1/1987 | Hazan et al. ................. | 356/339 |
| 4,854,705 | A | * | 8/1989 | Bachalo ....................... | 356/336 |
| 5,477,326 | A | * | 12/1995 | Dosmann .................... | 356/406 |
| 6,075,607 | A | | 6/2000 | Jinbo et al. | |
| 6,100,976 | A | * | 8/2000 | Ackerson .................... | 356/336 |
| 6,307,630 | B1 | * | 10/2001 | Banerjee ...................... | 356/436 |
| 6,320,661 | B1 | * | 11/2001 | Yoshida et al. .............. | 356/432 |
| 6,320,700 | B2 | | 11/2001 | Shiozawa | |

FOREIGN PATENT DOCUMENTS

| | | |
|---|---|---|
| DE | 41 09 469 A1 | 10/1991 |
| DE | 195 32 349 C1 | 8/1996 |
| DE | 100 50 349 C2 | 5/2002 |
| EP | 0 420 692 A2 | 4/1991 |
| EP | 0 866 331 A2 | 9/1998 |
| EP | 0 905 505 A1 | 3/1999 |
| EP | 0 908 716 A1 | 4/1999 |
| FR | 2 647 547 A1 | 11/1990 |
| JP | 10019727 A | 1/1998 |

(List continued on next page.)

OTHER PUBLICATIONS

C.K. Van Peski, et al, "Behavior of Fused Silica Irradiated by Low Level 193nm, Excimer Laser for Tens of Billions of Pulses," Proc. SPIE, vol. 4347, p. 177 et. seq. (2001).

Primary Examiner—Frank G. Font
Assistant Examiner—Sang H. Nguyen
(74) Attorney, Agent, or Firm—Sughrue Mion, PLLC

(57) ABSTRACT

A method and a device for determining the resistance of an optical material to radiation damage, wherein several sample volumes ($1a$, $1b$; $12_{11}$–$12_{33}$) within the optical material are simultaneously irradiated with test radiation having differing, measured or preset radiant-energy densities. The radiation employed for all sample volumes comes from a common radiation source (3; 13) and at least one parameter indicative of the resistances to radiation damage of the irradiated sample volumes is measured using measuring radiation. The measuring radiation also comes from the same radiation source that supplies the test radiation and the material's resistance to radiation damage is determined based on a functional relation between its radiation-damage-resistance parameter and the radiant-energy densities, wherein that functional relation is determined using the values of the radiation-damage-resistance parameters measured for the various sample volumes for the various radiant-energy densities employed. Such a method and device have application, e.g., in determining the resistances of $CaF_2$ and other optical materials to damage by ultraviolet laser radiation.

11 Claims, 2 Drawing Sheets

FOREIGN PATENT DOCUMENTS

| | | |
|---|---|---|
| JP | 10232184 A | 9/1998 |
| JP | 10232197 A | 9/1998 |
| JP | 11108794 A | 4/1999 |
| JP | 11108839 A | 4/1999 |
| JP | 11118669 A | 4/1999 |
| JP | 1123859 A | 8/1999 |
| JP | 11258108 A | 9/1999 |
| JP | 2000180301 A | 6/2000 |
| JP | 2001033379 A | 2/2001 |
| JP | 2001-099751 A | 4/2001 |
| JP | 2001099751 A | 4/2001 |
| JP | 2001099753 A | 4/2001 |

* cited by examiner

METHOD AND A DEVICE FOR DETERMINING THE RADIATION-DAMAGE RESISTANCE OF AN OPTICAL MATERIAL

The following disclosure is based on German Patent Application No. 102 25 842.2 filed on Jun. 4, 2002, which is incorporated into this application by reference.

BACKGROUND OF THE INVENTION

1. Field of the Invention

The invention relates to a method for determining the radiation-damage resistance of an optical material. More particularly, the invention relates to such a method that involves simultaneously irradiating several sample volumes of the optical material with test radiation from a common radiation source having differing, measured or preset, radiant-energy densities and measuring at least one parameter indicative of the radiation-damage resistances of the irradiated sample volumes using measuring radiation. The invention further relates to a device suitable for carrying out such a method.

2. Description of the Related Art

It is known that the optical quality of optical materials, i.e., materials, such as calcium fluoride or synthetic quartz glass, that serve a function in optical components, degrade over their service lives due to the aggregate radiation doses they have received. For example, the material's transmittance decreases over its service life due to the radiation dose it has received, a phenomenon that, in particular, also occurs in the case of applications involving ultraviolet laser radiation.

There is thus need for methods and devices that will allow determining the resistances of optical materials to damage due to irradiation to which they are subjected while in use in order to, e.g., allow predicting their service lives. A known method for obtaining meaningful results within reasonable measurement periods, which are orders of magnitude shorter than the typical service lives of optical materials, involves irradiating samples of the optical material involved employing radiant-energy densities that are significantly greater than those typically occurring in normal use. The results of measuring one or more parameters indicative of its resistance to radiation damage obtained over a range of such high radiant-energy densities are then extrapolated to the range of radiant-energy densities applicable to normal use in order to allow making statements regarding the radiation-damage resistance of the material in normal use and thus, e.g., regarding its maximum service life.

That extrapolation requires making several measurements employing various, high, radiant-energy-densities. The greater the total number of such measurements that are available and the more the radiant-energy levels employed differ from one another, the more reliably and meaningfully the measurement results obtained may be extrapolated to the interesting range of radiant-energy densities that typically occur in normal use. In that conjunction, a known method involves making several measurements on one or more samples of the optical material at various radiant-energy densities, where each of the various radiant-energy densities employed on a given sample is provided by its own, individual, radiation source, or by a single radiation source with an adjustable output that irradiates the samples consecutively, one after the other, with the various radiant-energy densities.

U.S. Pat. No. 6,075,607 describes a method and a device of that type for carrying out that method for model-based determination of the resistances of optical materials to damage by pulsed excimer-laser radiation, in which measurements of the absorption coefficients or transmittances, as parameters indicative of resistance to radiation damage, of a sample irradiated by differing energy densities are recorded over both a range in which linear functional dependence applies and a saturation region that corresponds to greater energy densities in order to then derive and correlate approximation equations yielding the functional dependence of those absorption coefficients or transmittances on irradiation energy density or the number of laser pulses using statistical and theoretical methods. The samples to be measured are preferably obtained by cleaving a large block.

Other methods and devices for determining the resistance of optical materials to radiation damage that involve conducting repeated measurements on a single sample, or various samples, using a test beam having the desired radiant-energy density for each of the measurements are disclosed in patent applications EP 0 905 505 A1, JP 2001-099753 A, JP 2000-099751 A, JP 2000-180301 A, JP 11-230859 A, JP 11-118669 A, JP 10-232184 A, and JP 10-232197 A.

Patent application JP 11-258108 A describes a method and a device for determining the resistance of an optical material to damage by laser radiation, in which a sample is repeatedly irradiated by a laser beam at differing radiant-energy densities and the absorbed portion is determined using a piezoelectric sensor each time it is irradiated, where the sample consists of a substrate and an optical coating in the form of an antireflective film or a reflective coating. In addition, a portion of the irradiation that is transmitted or reflected by this sample is directed to another sample consisting of the uncoated substrate material only. One additional sample can also be irradiated with the reflected and transmitted light, respectively. A lens may be arranged in front of each additional sample. The absorbed portion(s) of the radiation are also measured for one or both of these other samples using a piezoelectric sensor. The measurement results recorded for one or both of these other samples are then correlated to the measured values obtained for the coated sample in order to improve the accuracy of the relation governing the behavior of the latter.

The magazine article, C. K. Van Peski, et al: "Behaviour of Fused Silica Irradiated by Low Level 193 nm Excimer Laser for Tens of Billions of Pulses," Proc. SPIE, Vol. 4347, p. 177 (2001), presents the results of investigations of the behavior of synthetic quartz glass under irradiation by several tens of billions of pulses of excimer-laser radiation at a wavelength of 193 nm at low energy densities over extended time periods. For the purposes of those investigations, six samples of the quartz-glass material were lined up, one behind the other, on an associated test setup. The UV laser beam emitted by an ArF-laser was initially guided through the six samples lined up one behind the other as a first beam passing through a first volumnar zone, then deflected and guided back through the six samples in the reverse order as a second beam passing through a second volumnar zone, then redeflected and once again guided through the six samples as a third beam passing through a third volumnar zone, and, finally, redeflected again and guided back through the six samples as a fourth beam passing through a fourth volumnar zone, yielding a total of 24 sampled volumes, where the first sample volume irradiated by the first beam is irradiated by an energy density of 0.2 mJ/cm$^2$ and the other sampled volumes were successively irradiated with stepwise decreasing energy density. The investigation was done over a time period of 133 days, respectively interrupted for measurement procedures. During those measurement procedures, the effects of the irradiation on the material were investigated employing three different methods, firstly, interferometric measurements of wavefront distortions for transmitted radiation, secondly, birefringence measurements at a wavelength of 632 nm, and, thirdly, FTIR spectral analysis.

It is an object of the invention to provide a method and a device of the type mentioned at the outset hereof with which the resistance of an optical material to damage by radiation to which it is subjected in use may be comparatively reliably determined with relatively simple instrumentation in a relatively short time.

SUMMARY OF THE INVENTION

The invention achieves this and further objects by providing a method and a device for determining the resistance of an optical material to radiation damage having the characteristics that the measuring radiation comes from the same radiation source as the test radiation and the optical material's resistance to radiation damage is determined based on a functional relation between the damage-resistance parameter(s) and the radiant energy densities, which is determined from the values of the damage-resistance parameter(s) measured for the various sample volumes at the various radiant-energy densities.

In the case of the method according to the invention and the device according to the invention, several sample volumes of the optical material are simultaneously irradiated with test radiation that comes from the same radiation source, where the sample volumes are irradiated with test radiation having differing radiant-energy densities. One or more parameters, such as transmittance and/or absorptance, which are indicative of their resistances to radiation damage, are measured at the sample volumes using measuring radiation, which also comes from the one radiation source, and correlated to the radiant-energy density for the particular sample volume involved. This then allows determining the resistance of the optical material to radiation damage, based on a functional relation between that parameter and radiant-energy densities, which is determined using the measured values of the radiation-damage-resistance parameter of the various sample volumes for the various radiant-energy densities involved.

The invention thus allows very rapidly obtaining measured values of parameters representative of resistance to radiation damage at various radiant-energy densities using relatively simple instrumentation, in particular, using just a single radiation source, from which reliable statements regarding the resistance of the optical material to radiation damage and thus also regarding, e.g., its expected service life in normal use, where radiant energy densities that are much less than that of the test radiation employed are usually employed, after a relatively short time, particularly if high energy densities are employed. When making such service-life estimates, the functional relation that expresses one or more radiation-damage-resistance parameters as a function of radiant-energy density that was determined during testing, preferably for a range of high energy densities, may be extrapolated to the range of energy densities that apply during normal use of the optical material. That extrapolation is preferably performed with the aid of a model.

Under another embodiment of the invention, the measuring radiation is coupled out of the respective sample volume involved in the form of a portion of the test radiation, i.e., the measurement is performed simultaneously with the irradiation by making use of the test radiation.

The sample volumes may be portions of a single test sample, i.e., test radiation passes through the test sample and the one or more radiation-damage-resistance parameters are then measured at several partial volumes of the test sample that follow one another in the beam path.

Alternatively, or additionally, sequential arrangements of sample volumes of separate test samples sequentially arrayed, one after the other, along the beam path traversed by the test radiation may be formed. Under a beneficial configuration of this measure, a variable attenuator, with which the radiant-energy density of the test radiation may be variably attenuated in a controlled manner, is arranged between each pair of sequentially arrayed test samples. Employment of such attenuators will allow maintaining the energy densities at the various sample volumes substantially constant at their differing, initial, values over the full duration of testing, even though test-radiation energy-density losses at the sample volumes will, in general, decrease over that period of time due to radiation-induced aging of the material involved, which may be compensated by setting the attenuators to greater attenuation factors at the start of testing and then resetting them to lesser attenuation factors as testing progresses.

Under another embodiment of the invention, transmittance is employed as a radiation-damage-resistance parameter. The transmittances of the respective sample volumes are either determined from the transmitted fractions of the test radiation or measured using a measuring beam directed at the sample volumes.

BRIEF DESCRIPTION OF THE DRAWINGS

Beneficial embodiments of the invention are depicted in the figures and will be described below, where those figures depict.

DETAILED DESCRIPTION OF PREFERRED EMBODIMENTS

Figure 1:
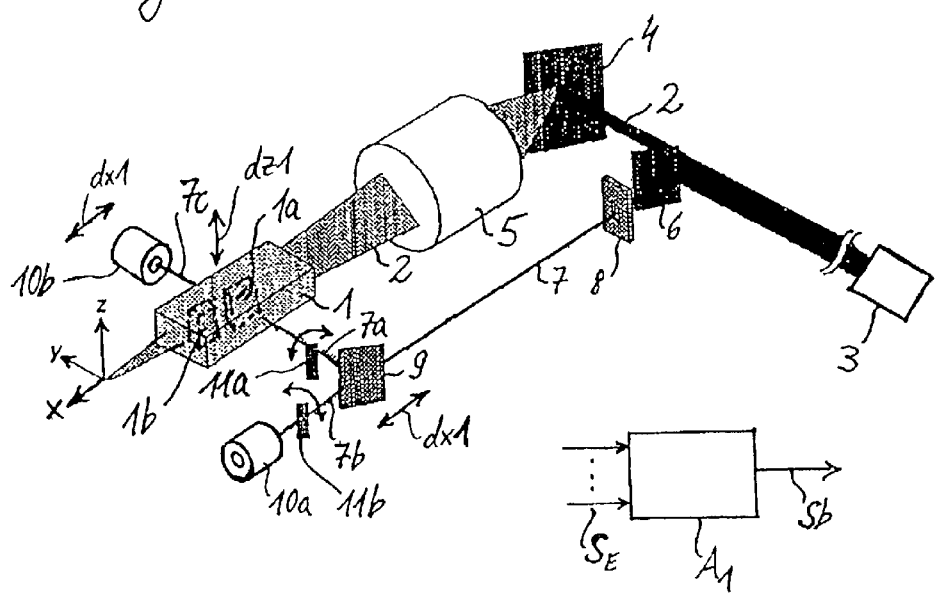
FIG. 1 a schematized perspective view of a device for determining the resistance of an optical material to damage by laser radiation, based on resistance testing conducted on several partial volumes of a test sample.

The device shown in FIG. 1 is used for determining the resistance of an optical material, such as calcium fluoride or quartz glass, to damage by laser radiation in order to, e.g., arrive at statements regarding the expected service lives of optical components, such as mirrors, lenses, and similar, that are fabricated from that material and subjected to the associated laser radiation in normal use, where the laser radiation involved may be, in particular, laser light falling within the visible or UV spectral regions. In order to determine that resistance to radiation damage, in the case of that device shown in FIG. 1, a single, e.g., cubical, test sample 1 is transited by a test beam 2 generated by a laser 3. The test beam is formed by guiding it through a beam-expander unit equipped with a spherical mirror or a paraboloidal mirror 4 and a lens assembly 5, from which it emerges with a broadened, convergent beam profile and passes through the test sample 1.

A scanning beam 7 parallel to the test beam 2 that is formed by an aperture stop 8 is coupled out of the light beam emitted by the laser 3 by a beamsplitter 6. Another semitransmitting mirror 9 splits the scanning beam 7 into two partial beams 7a and 7b, where the transmitted partial beam 7b is guided to a first beam-energy-density measurement unit 10a that may be used for measuring the radiant-energy density of this transmitted partial beam 7b, and thus also that of the partial beam 7a reflected by the semitransmitting mirror 9, using the previously determined or known beam-splitting ratio of the semitransmitting mirror 9. The reflected partial beam 7a then forms the measuring beam, which is directed at the test sample 1 along a y-direction that is orthogonal to the x-direction of the test beam 2. That portion 7c of the measuring beam that is transmitted by the test sample 1 is guided to a second radiant-energy-density measurement unit 10b. The transmittance of the partial volume of the test sample 1 transited by the test beam 2 and the measuring beam 7a may then be determined from the signals from both measurement units 10a and 10b.

Other components of the test setup shown in FIG. 1 are two computer-controlled, movable, stops 11a and 11b for optionally blocking the measuring beam 7a and/or the transmitted scanning beam 7b. The test setup is also located in a conventional, enclosed, test chamber that is not shown here, through which a suitable flushing gas, e.g., nitrogen, is conducted in order to provide for sufficient freedom from contamination.

If necessary, one or more additional radiant-energy-density measurement units may be employed in a manner not explicitly shown in order to determine, e.g., the radiant-energy density of the light emitted by the laser 3 and/or that of the scanning beam 7 split off therefrom from direct measurements.

A critical fundamental idea underlying the arrangement shown in FIG. 1 is that of measuring the dependence of the transmittances of several partial volumes of the test sample 1 that lie one behind the other, of which two test volumes 1a and 1b have been symbolically indicated and drawn oversize, rather than to scale, in FIG. 1 in order to make them more clearly recognizable, on the energy density incident thereon. To that end, certain components of the test setup are arranged on, e.g., an x-y translation stage that is moveable along the z-direction, such that they may be accurately brought to various set positions in order to scan the respective individual sample volumes of the test sample 1. In particular, the semitransmitting mirror 9 and the measurement unit 10b for measuring the transmitted portion 7c of the measuring beam are arranged such that they are translatable along the x-direction, as indicated by double-headed arrows dx1 shown in FIG. 1, which will allow one group after another of the sample volumes arrayed one behind the other along the direction x of the test beam to be scanned by the measuring beam 7a. In order to scan several groups of partial volumes of the test sample 1 that are arrayed, one above the other, along the z-direction, the height of the test sample is translatable along the z-direction, as is indicated in FIG. 1 by an associated double-headed arrow dz1.

In the case of the example depicted in FIG. 1, as shown therein, the test beam 2 from the optical system 4, 5 situated ahead of the test sample 1 is set up to have a flat profile along the z-direction and a slightly convergent profile along the x-y-direction within the test sample 1. Each sample volume arrayed one above the other in the z-direction is thus correlated to the same radiant-energy density from the test beam 2, which will allow improving analytical-error statistics. Sample volumes that follow one another along the direction of the test beam 2 are irradiated by radiant-energy densities that decrease along the direction x of the test beam 2, since only that portion that has been reduced by absorption and/or scattering losses and transmitted by the preceding sample volume reaches the next sample volume. However, since the beam convergence that has been set partially compensates for this effect, the respective final sample volumes along the direction x of the test beam will also be irradiated by sufficiently high, analyzable, energy densities from the test beam 2.

When testing resistance to radiation damage, the test sample 1 is thus raised to a certain initial height along the z-direction by the setup shown in FIG. 1, which causes a first group of sample volumes arrayed one behind the other to be irradiated, one after the other, by the test beam 2 and scanned by the measuring beam 7a in order to determine the behaviors of their transmittances, to which end the latter beam scans the various sample volumes in rapid sequence. It should be obvious that alternatively scanning all of those sample volumes simultaneously will also be possible if the measuring beam 7a is split up into a corresponding number of parallel measuring beams and a corresponding number of radiant-energy-density measurement units 10b is arranged next to one another. Once this first group of sample volumes has been measured, the test sample 1 is then relocated along the z-direction in order to allow measuring the dependence of the transmittances of a second group lying above or below the first group along the direction x of the test beam on radiant-energy density. This procedure is then repeated until the entire volume of the test sample 1 has been covered.

The transmittances measured on the test sample 1 at various irradiation levels, i.e., various radiant-energy densities, in this manner for a number of sample volumes are analyzed by an analyzer unit $A_1$ that determines the resistance of the optical material of the test sample 1 to radiation damage, where the measured values and, if necessary, additional input data are supplied to it in the form of input signals $S_E$. It provides the radiation-damage-resistance data $S_b$ sought at its output. An algorithm, in particular, a model-aided algorithm, may be implemented in the analyzer unit $A_1$. Such a model-aided simulation may, in practice, get by with measured values obtained for three differing radiant-energy densities, e.g., 0.5 mJ/cm$^2$, 1.5 mJ/cm$^2$, and 5 mJ/cm$^2$, where recording measured values obtained at a significantly higher number of differing radiant-energy densities will be preferable in order to improve the reliabilities and accuracies of the model-aided analyses. In modeling, it may prove helpful to verify that a stationary state has been reached or to irradiate samples with a prescribed minimum number of laser pulses of the order of, e.g., 2×10$^9$ pulses. Since that portion of the test beam that is transmitted by the respective sample volume may be determined based on a simultaneous measurement of its transmittance using the measuring beam 7a and the former's beam profile, e.g., the convergent profile set in FIG. 1, is known, the decreasing radiant-energy densities along the direction x of the test beam for the individual sample volumes lined up one behind the other may be determined therefrom.

The analyses include determining a functional relation between the transmittance and radiant-energy density over the range of high radiant-energy densities employed in test procedures using the test beam 2, based on the measurement results obtained therefrom and extrapolation of those functional relations determined to the range of lower radiant-energy densities. The optical material involved is subjected to such lower radiant-energy densities in normal use, where it is employed for fabricating, e.g., the mirrors and lenses of optical systems for guiding laser beams whose wavelength corresponds to that of the test beam 2.

Figure 2:
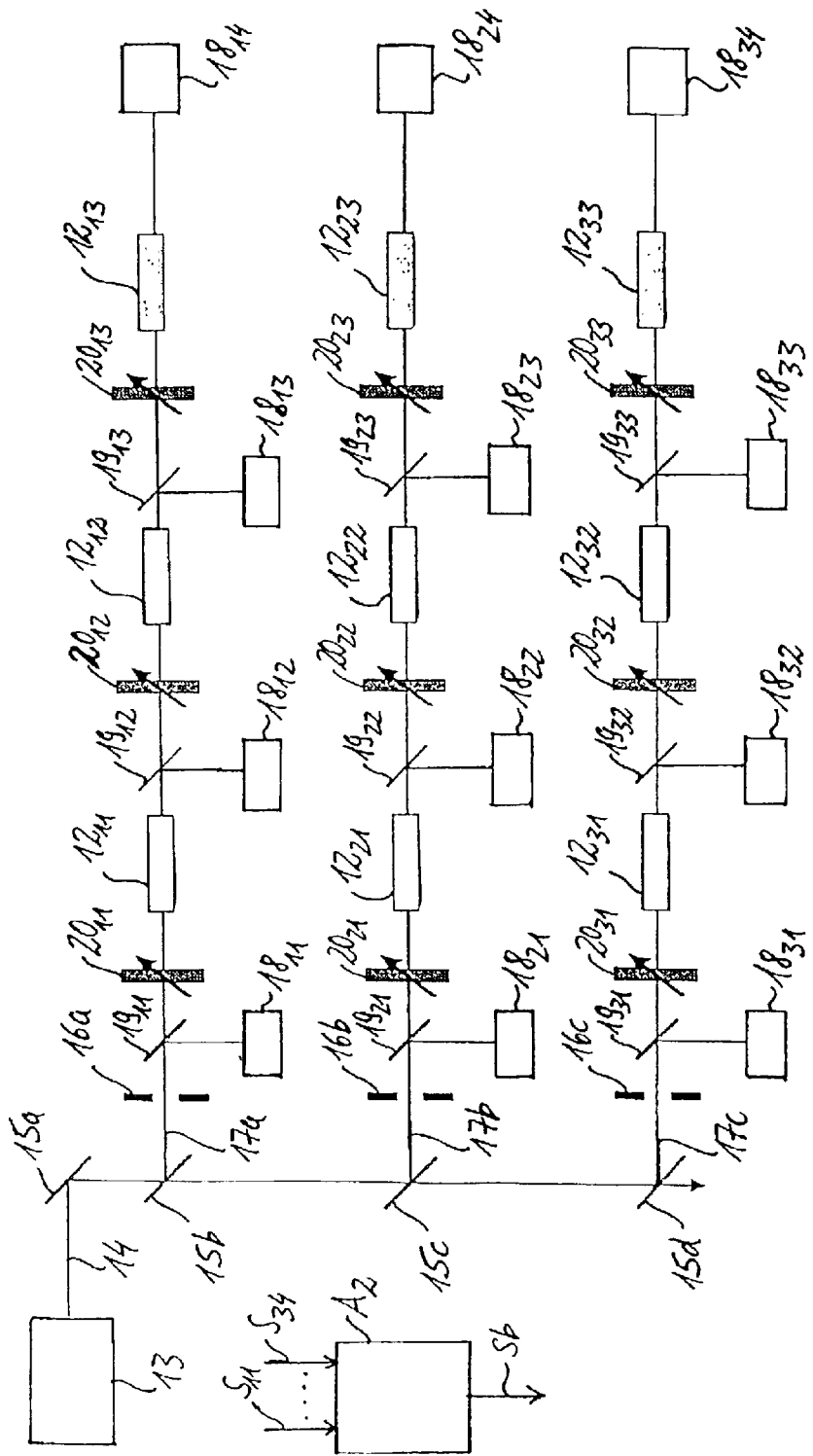
FIG. 2 a block schematic of another device for determining the resistance of an optical material to damage by laser radiation, based on resistance testing conducted on several parallel groups of individual test samples that are lined up, one after the other, in the respective beam paths and have attenuators allocated to them.

FIG. 2 depicts a test setup for determining the resistance of an optical material to radiation damage in which individual test samples arranged in several parallel, irradiated, rows of test samples arranged one behind the other that form the several sample volumes under test. As an example, FIG. 2 depicts the case of three similarly configured rows, each of which contains three test samples $12_{11}$–$12_{13}$, $12_{21}$–$12_{23}$, and $12_{31}$–$12_{33}$ that are lined up, one behind the other, and irradiated in turn.

The test radiation is once again supplied by a single laser source 13 having an associated optical system. Test beams 17a–17c, one for each row of test samples, formed by a respective one of several aperture stops 16a–16c are coupled out from its emitted laser beam 14 by a series of semitransmitting mirrors 15a–15d. The test beams 17a–17c that are coupled out thus have different energy densities decreasing with increasing distance from the laser source 13. The radiant-energy densities of each of the individual test beams 17a, 17b, 17c are measured at the exits of the aperture stops and again by one of the measuring units $18_{11}$–$18_{34}$ after they have transited one of the test samples $12_{11}$–$12_{33}$, which is why a defined portion of the measuring beam is coupled out by semitransmitting mirrors $19_{11}$–$19_{33}$ following each of the aperture stops 16a, 16b, 16c and following each of the test samples, with the exception of the final test sample in the row.

In the case of the test setup depicted in FIG. 2, the test radiation thus simultaneously serves as measuring radiation, in that that portion of test radiation transmitted by each test sample $12_{11}$–$12_{33}$ is detected by the measuring units $18_{11}$–$18_{34}$. In order to fully compensate for, or at least largely compensate for, any decreases in the transmittances of the test samples $12_{11}$–$12_{33}$ caused by aging due to their being irradiated at high energy densities by the test beams 17a, 17b, 17c a variable attenuator $20_{11}$–$20_{33}$ is arranged in front of each test sample $12_{11}$–$12_{33}$. These attenuators $20_{11}$–$20_{33}$ are initially set to relatively high attenuation factors and then reset to correspondingly lower attenuation factors during the course of testing procedures in the event that any declines in the transmittances of the test samples that follow them in the optical train are observed. In this manner, each test sample is thus provided with a radiant-energy density that remains largely constant throughout the entire course of testing procedures, even if the transmittances of the individual test samples $12_{11}$–$12_{33}$ should decrease. Instead of the positioning of the attenuators $20_{11}$–$20_{33}$ between each of the semitransmitting mirrors $19_{11}$–$19_{33}$ and the associated test samples $12_{11}$–$12_{33}$ shown in FIG. 2, they might also be arranged at any other suitable location in the beam paths of the respective measuring beams, in particular, following each of the test samples $12_{11}$–$12_{33}$.

Figure 3:
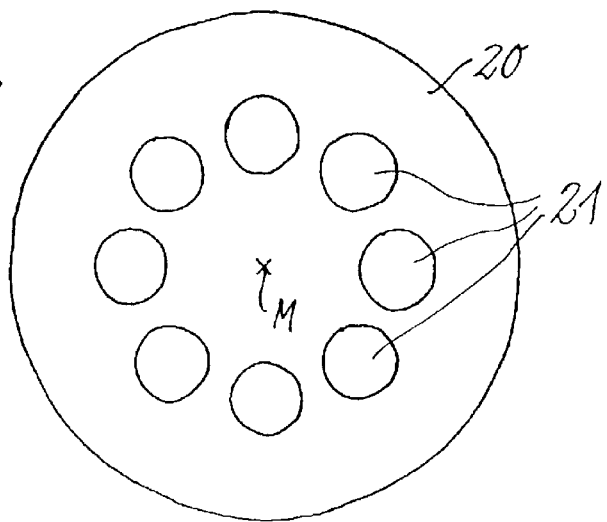
FIG. 3 a schematized top view of one of the attenuators shown in FIG. 2.

The attenuators $20_{11}$–$20_{33}$ may be of a type schematically depicted in a top view in FIG. 3. The attenuator 20 depicted in FIG. 3 consists of a disk that is rotatable about its center M, into which circular attenuation zones 21 whose centers lie on a common circle centered on the disk's center have been formed. These attenuation zones 21 have attenuation factors for laser radiation that is transmitted by them that differ from one another and may be individually brought into the paths of the respective test beams 17a, 17b, 17c of the arrangement shown in FIG. 2 by rotating the disk 20. These attenuation zones 21 may be fabricated from, for example, $CaF_2$ or similar materials, by matting their surfaces to varying degrees. This matting of the surface of each attenuation zone may be accomplished by a conventional method, in which case, their respective transmittances will then be determined by, e.g., calibrations. Beneficial implementations include attenuation zones fabricated from a plate matted on one side only or two plates matted on one side only assembled with their matted sides spaced at a distance from one another and facing one another. In the case of the latter embodiment, the matted surfaces are isolated from the ambient and thus shielded from dirt. Other options for these attenuators include a single window or a stack of several, thin, polished, windows fabricated from, e.g., $CaF_2$. All of these implementations share the beneficial property that attenuators of this type do not significantly degrade during test procedures.

The further analysis of the testing results obtained for the test samples $12_{11}$–$12_{33}$ using the test setup shown in FIG. 2 in order to determine the resistance to radiation damage of the optical material to be tested corresponds to that explained above for the case of the test setup shown in FIG. 1. In the case of the example depicted in FIG. 2, all test samples $12_{11}$–$12_{33}$ are irradiated throughout the testing time by test beams 17a, 17b, 17c having largely constant radiant-energy densities that differ from one another. Consequently, each of the test samples $12_{11}$–$12_{33}$ yields a transmittance data point indicative of resistance to radiation damage as a function of radiant-energy density over the range of high radiant-energy densities employed for the test radiation. If the shape and energy density of the emitted laser beam 14 remain constant, then nine data points covering the functional relation between its transmittance and the total radiation dose to which it has been exposed will be simultaneously obtained using the test setup depicted in FIG. 2.

This may already be sufficient to determine the resistance of the optical material to radiation damage over the range of lower radiant-energy densities typically encountered in normal use using, e.g., model-aided extrapolations of the relation derived from the nine data points obtained at higher energy densities, in the manner explained above. If necessary, the number of data points may be multiplied by providing more than three parallel rows of test samples irradiated by test radiation and/or more than three test samples per row, or by varying the radiant-energy density of the emitted laser beam 14, combined with measuring and analyzing another set of, e.g., nine, data points, at a different laser output power, if necessary. In the case of simplified implementations, it may be sufficient to provide just one or two parallel rows, each containing at least two test samples that are irradiated one after the other.

An analyzer unit $A_2$ that receives the necessary input data, in particular, the output signals $S_{11}$–$S_{34}$ from the respective radiant-energy-density measurement units $18_{11}$–$18_{34}$, analyzes that data in order to derive therefrom the radiation-damage-resistance data $S_b$ sought, as explained above.

As will be evident from the foregoing descriptions of beneficial sample embodiments, the invention allows relatively rapidly and accurately determining the resistance of an optical material to radiation damage by simultaneously irradiating several sample volumes with test radiation having measured or preset radiant-energy densities that differ for the various respective sample volumes, where only a single radiation source is needed for supplying both the test radiation and measuring radiation. One or more parameters that are indicative of the resistance of the optical material to radiation damage is/are measured at each irradiated sample volume. The parameter(s) involved may be their transmittance, as in the case of the examples presented above, and/or other parameters, such as their absorptance, where hybrid forms of the sample embodiments shown in FIGS. 1 and 2, wherein several test samples are arranged in the manner shown in FIG. 2 and several sample volumes of each test sample are measured in the manner shown in FIG. 1, are also feasible. In addition to the sample embodiments shown, which employ transmittance measurements, embodiments that employ reflectance measurements, i.e., embodiments wherein each sample volume, commencing with the second sample volume, is irradiated by radiation reflected by a sample volume that precedes it in the optical train, are also feasible. Moreover, the convergent beam employed for irradiating test samples shown in FIG. 1 may be replaced by a beam having any other beam geometry, if necessary.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all changes and modifications as fall within the spirit and scope of the invention, as defined by the appended claims, and equivalents thereof.

What is claimed is:

1. A method for determining the resistance of an optical material to radiation damage, comprising:
   irradiating several sample volumes of the optical material simultaneously by test radiation having various differing radiant-energy densities, wherein the test radiation for all of the sample volumes comes from a common radiation source,
   measuring at least one parameter indicative of the respective resistances to radiation damage of the sample volumes, wherein the measuring radiation comes from the same radiation source as the test radiation, and
   determining the optical material's resistance to radiation damage based on a functional relation between that damage-resistance parameter and the radiant energy densities, wherein the functional relation is determined from the values of the damage-resistance parameter measured for the several sample volumes at the various radiant-energy densities.

2. A method according to claim 1, wherein the measuring radiation is created by coupling a portion of the test radiation out from the respective sample involved.

3. A method according to claim 2, further comprising:
   providing the several sample volumes sequentially arranged in one or more parallel, irradiated branches of the test radiation, and
   holding the radiant-energy density transiting each of the sample volumes substantially constant over the duration of testing by variable attenuators, each of which is assigned to a particular one of the sample volumes.

4. A method according to claim 1, wherein several subvolumes of the sample involved are employed as the sample volumes.

5. A method according to claim 1, wherein transmittance is employed as the radiation-damage parameter, and either test radiation incident on each of the sample volumes or a separate measuring beam directed at each of the sample volumes serves as the measuring radiation.

6. A device for determining the resistance of an optical material to radiation damage comprising:
   means for simultaneously irradiating several sample volumes of the optical material with test radiation from a common radiation source having various differing radiant-energy densities,
   means for measuring at least one parameter indicative of the damage-resistance of the irradiated sample volumes and employing measuring radiation,
   wherein the source that supplies the test radiation also supplies the measuring radiation, and
   wherein the measuring means include analytical facilities for determining a functional relation between the damage-resistance parameter and the radiant energy densities employing the values of the damage-resistance parameter measured at the several sample volumes for the various radiant-energy densities and for determining the optical material's resistance to radiation damage based on the functional relation determined.

7. A device according to claim 6, further comprising means for coupling out a portion of the test radiation for use as the measuring radiation.

8. A device according to claim 7, further comprising a setup for irradiating a sample with test radiation and measuring the damage-resistance parameter of the several sample volumes of the sample.

9. A device according to claim 7, further comprising a setup for irradiating several, individual samples sequentially arranged along a path traversed by test radiation, wherein each of the individual samples has a variable attenuator assigned to it.

10. A device according to claim 6, wherein the means for measuring resistance to radiation damage are configured for measuring the transmittance of each of the sample volumes by acquiring the transmitted portion of the test radiation incident on each of the sample volumes or of a separate measuring beam directed at each of the sample volumes.

11. A device, comprising:
   a radiation source irradiating a plurality of samples of optical material with test radiation having various differing radiant-energy densities and with measurement radiation measuring at least one parameter indicative of a radiation damage resistance for each of the various radiant-energy densities, and
   an analyzer calculating a resistance to radiation damage in accordance with the radiant-energy densities and measured values for the radiation damage parameter for each of the samples at each of the radiant-energy densities.

* * * * *